United States Patent
Sakaue

(10) Patent No.: US 9,529,975 B2
(45) Date of Patent: Dec. 27, 2016

(54) MEDICAL INFORMATION PROCESSING SYSTEM AND MEDICAL INFORMATION PROCESSING APPARATUS

(71) Applicant: Toshiba Medical Systems Corporation, Otawara-shi (JP)

(72) Inventor: Kousuke Sakaue, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 16 days.

(21) Appl. No.: 13/778,327

(22) Filed: Feb. 27, 2013

(65) Prior Publication Data

US 2013/0226615 A1 Aug. 29, 2013

(30) Foreign Application Priority Data

Feb. 27, 2012 (JP) .................................. 2012-039509

(51) Int. Cl.
*G06Q 50/00* (2012.01)
*G06F 19/00* (2011.01)

(52) U.S. Cl.
CPC ............. *G06F 19/36* (2013.01); *G06F 19/322* (2013.01)

(58) Field of Classification Search
CPC ......... G06Q 50/22; G06Q 50/24; G06F 19/36; G06F 19/322; G06F 19/3406; G06F 19/3418
See application file for complete search history.

(56) References Cited

U.S. PATENT DOCUMENTS 6,370,533 B1   4/2002   Sato et al.

FOREIGN PATENT DOCUMENTS

| CN | 102063461 A | 5/2011 |
|---|---|---|
| JP | 08-044796 | 2/1996 |
| JP | 09-065436 | 3/1997 |
| JP | 2002-238919 | 8/2002 |
| JP | 2005-025556 | 1/2005 |
| JP | 4405172 | 11/2009 |

(Continued)

OTHER PUBLICATIONS

Office Action issued Oct. 20, 2015, in Japanese Patent Application No. 2012-039509, filed Feb. 27, 2012.

(Continued)

*Primary Examiner* — Michelle L Le
(74) *Attorney, Agent, or Firm* — Oblon, McClelland, Maier & Neustadt, L.L.P.

(57) ABSTRACT

A medical information processing system including an input part, a sound analyzer, a state detector, determination information storage, and an association processor. Upon receiving plural types of medical information via sound input respectively, the medical information processing system can distinguish the plural types of medical information by a simple operation. The input part receives the medical information via sound input. The sound analyzer analyzes the received sound and converts it into character strings. The state detector detects plural states of the input part, respectively. The determination information storage stores in advance determination information in which each of plural states is related to types of information making up a medical record. The association processor identifies the type corresponding to the detected state based on the determination information, and relates the information indicating the identified type with the character strings converted from the sound input.

4 Claims, 8 Drawing Sheets

(56) References Cited

FOREIGN PATENT DOCUMENTS

JP         2010-113519         5/2010

OTHER PUBLICATIONS

Office Action issued Nov. 5, 2015, in Chinese Patent Application No. 201310187769.4.
"Voicekarte" Development of Voicekarte, Medical Care and Computer, Japan, Kabushiki Kaisha Japan Electronic Publishing, Mar. 20, 1998, vol. 9, No. 3, pp. 127-133.

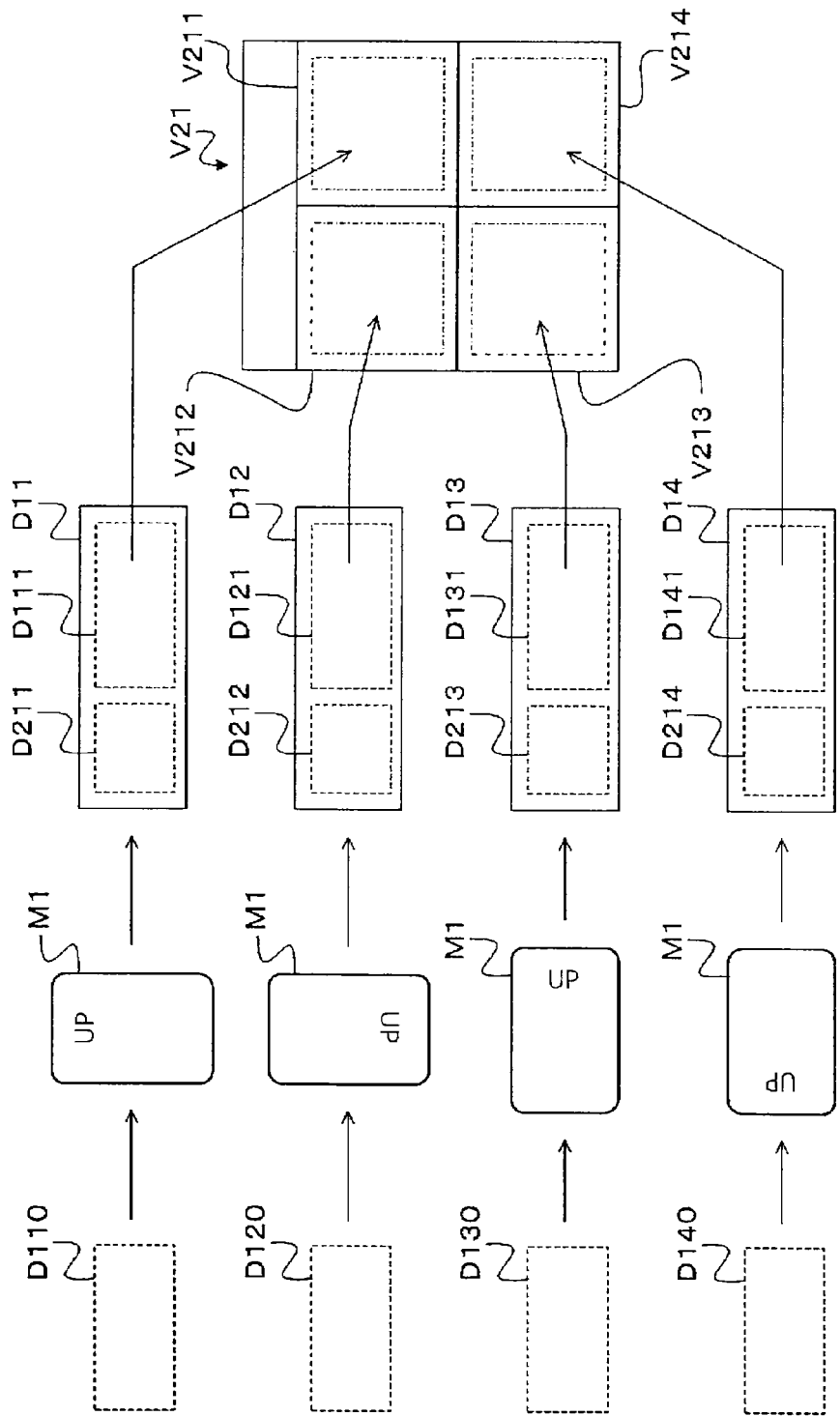

MEDICAL INFORMATION PROCESSING SYSTEM AND MEDICAL INFORMATION PROCESSING APPARATUS

CROSS-REFERENCE TO RELATED APPLICATION

This application is based upon and claims the benefit of priority from Japanese Patent Application No. 2012-039509, filed on Feb. 27, 2012; the entire contents of which are incorporated herein by reference.

FIELD

The present embodiment pertains to technology for assisting with the generation and updating of medical records made up of a plurality of types of medical information.

BACKGROUND

Wireless communication has been put to practical use, and recently, medical information such as patient information and examination information managed and stored by a server can be transmitted and received to and from a portable compact terminal (namely, a mobile terminal). Depending on the spread of such a mobile terminal, regardless of time and place, it becomes possible to generate and update medical records such as electric medical charts and diagnostic reports using a mobile terminal.

In addition, technology for converting sound information into character strings has been put to practical use. Thereby, for example, in receiving medical information including medical findings as sound input, it becomes possible to convert this into character strings and input these character strings into medical records.

On the other hand, in medical records such as electric medical charts and diagnostic reports, it is necessary to distinguish between and input a variety of information. Such information includes, for example, subjective information such as the main complaint and other complaints of patients (hereinafter, referred to as "main complaint"), objective information such as physical findings and examination findings (hereinafter, referred to as "findings"), assessment and analysis results (hereinafter, referred to as "assessment"), and planning of examination and therapies (hereinafter, referred to as "planning"). In the case of inputting such information through a mobile terminal, it is necessary to specify the types of input information or the destination into which the information is input via screen operations and key inputs, etc.

BRIEF DESCRIPTION OF THE DRAWINGS

FIG. 2 illustrates an example of the operation of the medical information processing system according to the embodiment.

DETAILED DESCRIPTION

This embodiment was created with the objective of respectively receiving a plurality of types of medical information via sound input, and making it possible to distinguish this medical information by a simple operation.

In order to achieve the above-described object, this embodiment describes a medical information processing system for inputting medical information comprising an input part, a sound analyzer, a state detector, a determination information storage, and an association processor. The input part is provided in a terminal device and receives medical information via sound input. The sound analyzer analyzes the received sound and converts it into character information. The state detector detects the state of the terminal device. The determination information storage stores in advance determination information in which a plurality of states with respect to the terminal device are related to each type of a plurality of parts making up medical records. The association processor identifies the type corresponding to the state of the detected terminal based on the determination information, and relates the information indicating the identified type with the character information converted from the sound input.

Figure 1A:
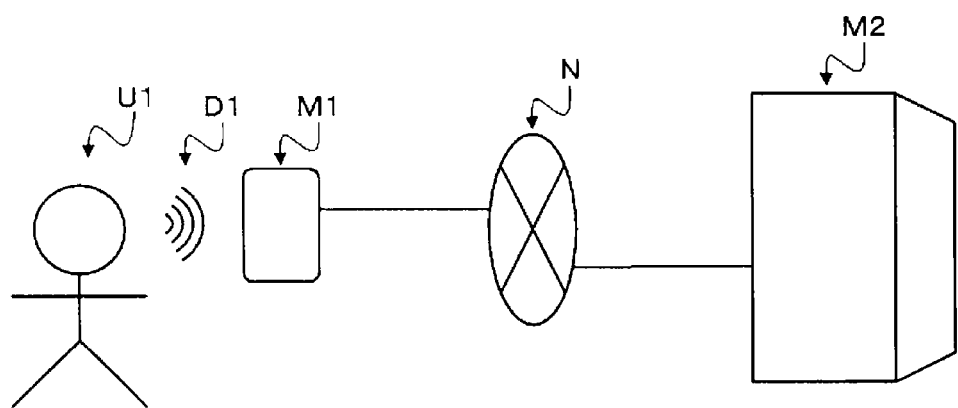
FIG. 1A illustrates the configuration of a medical information processing system according to the embodiment.
Figure 1B:
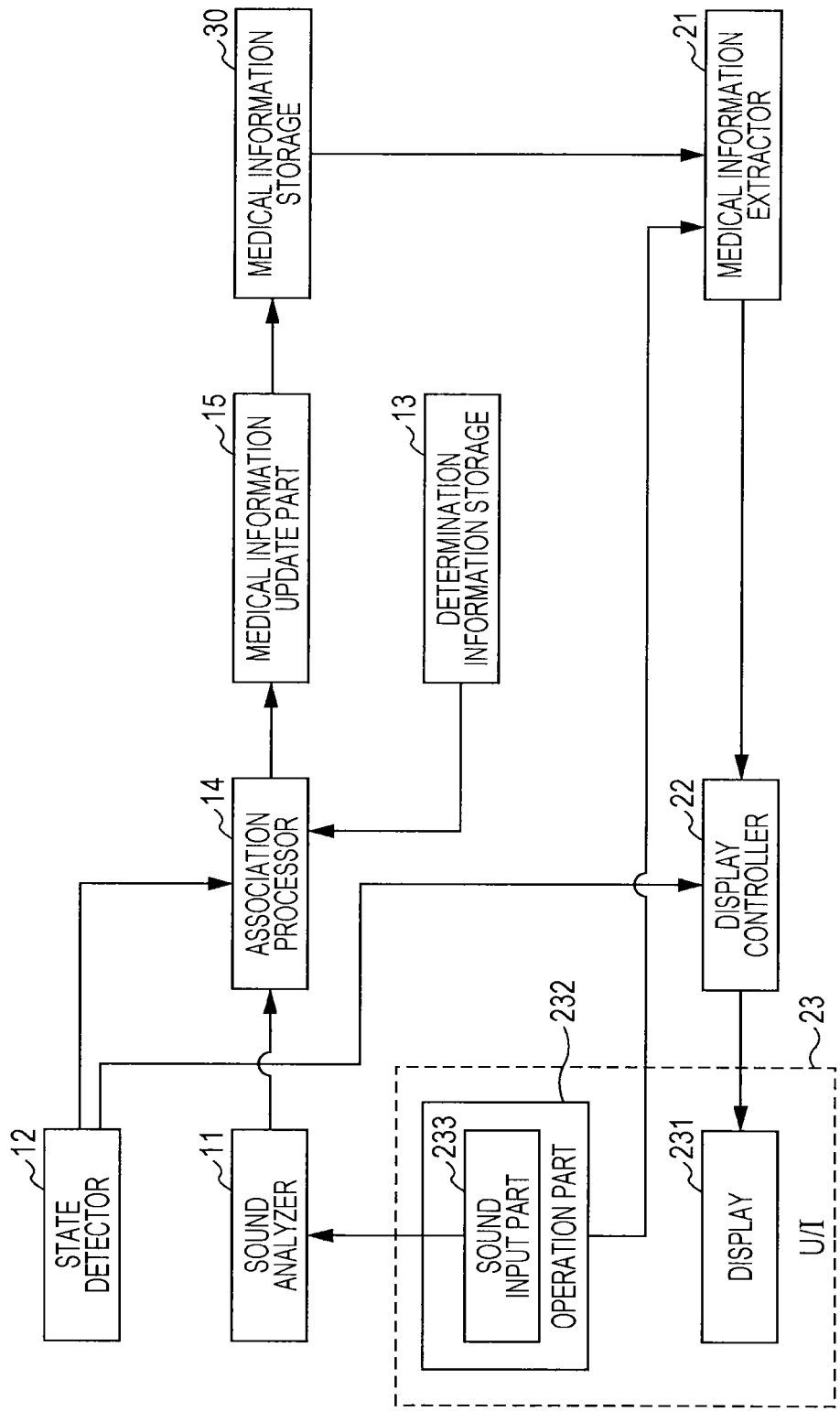
FIG. 1B is a block diagram of the medical information processing system according to the embodiment.

A medical information processing system according to the present embodiment will be described with reference to FIG. 1A and FIG. 1B. At first, FIG. 1A will be referred. As illustrated in FIG. 1A, in the medical information processing system according to the present embodiment, a mobile terminal M1 and a medical information management server M2 are connected via a network N. The mobile terminal M1 is an input device for inputting medical information. In addition, the medical information management server M2 is a server for managing and storing the input medical information and medical records such as electric medical charts and diagnostic reports created based on this medical information. An operator U1 inputs medical information into the mobile terminal M1 as sound data D1. The mobile terminal M1 converts the sound data D1 into character string data, and manages and stores this as medical information in the medical information management server.

Upon receiving the medical information via the sound input as sound data D1, the medical information processing system according to the present embodiment recognizes the types of medical information input at the time in accordance with the physical direction of the mobile terminal M1. For example, when the mobile terminal M1 is turned up, the medical information processing system recognizes the sound data D1 input at the time as information indicating "a main complaint." Thus, by associating the direction of the mobile terminal M1 and the type of information (for example, "a main complaint," "findings," "assessment," and "planning") with each other in advance, the medical information processing system simultaneously recognizes the type of sound data D1 based on the physical direction of the mobile terminal M1. Hereinafter, the specific configurations for carrying out such operations will be described with reference to FIG. 1B. The medical information processing system according to the present embodiment comprises a sound analyzer 11, a state detector 12, determination information storage 13, an association processor 14, a medical information update part 15, medical information storage 30, medical information extractor 21, a display controller 22, and a U/I23. Further, the places on which these configurations are displaced are not limited if they can carry out the respective functions to be described later, and they may be displaced on either of the mobile terminal M1 or the medical information management server M2.

The U/I23 is a user interface (User Interface) including a display 231 and an operation part 232. The display 231 displays an operational screen for inputting medical information and the selected medical record. The operation part 232 is an operation part that carries out the operations for selecting the medical record to be displayed and inputting the medical information. In addition, the operation part 232 includes a sound input part 233. The sound input part 233 is an input part for inputting the medical information as sound data (namely, carrying out sound input). The sound input part 233 outputs the sound data input from the operator to the sound analyzer 11.

The sound analyzer 11 receives sound data from the sound input part 233. The sound analyzer 11 analyzes this sound data and converts it into character string data. Further, the sound analyzer 11 may correct any description fluctuations caused by homonyms, etc. by carrying out syntax analysis (for example, lexical analysis and semantic analysis) on this character string data. The sound analyzer 11 relates information indicating a timing point upon receiving the sound data as the generation origin of the character string data to the generated character string data. In this way, by relating the information indicating the timing point to the character string data, the medical information processing system itself can recognize at which timing point each character configuring the character string information is input. The sound analyzer 11 outputs the character string data to which the information indicating the timing point is related to the association processor 14.

It should be noted that the sound analyzer 11 may be installed on an external server (not shown), on neither of the mobile terminal M1 nor the medical information management server M2. In this case, the sound data in the sound input part 233 is sent to this external server so that the sound analyzer 11 provided on this external server analyzes the sound data to transform the sound data into the character string data. The transformed character string data is sent to the association processor 14 on either of the mobile terminal M1 or the medical information management server M2. As set forth, it is possible to adopt a configuration of externally installing the sound analyzer 11.

The state detector 12 detects the physical direction of the mobile terminal M1. Specifically, the mobile terminal M1 comprises a gyro, a vibration sensor, an acceleration sensor, etc. Therefore, the state detector 12 analyzes outputs of these sensors, and detects the physical direction of the mobile terminal Ml. The state detector 12 relates the information indicating the timing point upon receiving output from each sensor indicating the physical direction to the information (hereinafter, referred to as "the state information") indicating the physical direction of the detected mobile terminal M1 (namely, the state of the mobile terminal M1). Thereby, the medical information processing system itself can recognize, for example, changes in the physical direction of the mobile terminal M1 in accordance with the timing point. The state detector 12 outputs the state information to which the information indicating the timing point is related to the association processor 14.

The determination information storage 13 stores in advance the determination information in which the state information (namely, information indicating the physical direction of the mobile terminal M1) is related in advance to information (hereinafter, referred to as "information type") indicating the type of information (for example, "main complaint," "findings," "assessment," and "planning").

The association processor 14 receives character string data from the sound analyzer 11. In addition, the association processor 14 receives state information from the state detector 12. The association processor 14 compares the state information with the determination information stored in the determination information storage 13, and identifies the type of information corresponding to this state information. The association processor 14 relates the identified information type to the character string data.

With reference to FIG. 2, the operation of this association processor 14 will be described with specific examples. FIG. 2 is a conceptual drawing illustrating an example of the operation of the medical information processing system according to the present embodiment. In FIGS. 2, D110 to D140 illustrate sound data. In addition, character string data converted from the sound data D110 to D140 respectively by the sound analyzer 11 is defined as character string data D111 to D141, respectively. In addition, D211 to D214 respectively indicate different types of information. Here, a description will be given assuming that the information types D211, D212, D213, and D214 correspond to "main complaint," "findings," "assessment," and "planning," respectively.

As illustrated in FIG. 2, the association processor 14 receives the state information corresponding to this state from the state detector 12 when the mobile terminal M1 turns up. In addition, the association processor 14 receives the character string data D111 converted from the sound data D110 input in this case from the sound analyzer 11. The determination information storage 13 compares the state information with the determination information stored in the determination information storage 13, and identifies the information type D211. The determination information storage 13 relates the information type D211 to the character string data D111. The character string data D111 to which this information type D211 is related is defined as medical data D11. Similarly, the association processor 14 identifies "information type D212" when the mobile terminal M1 turns down, identifies "information type D213" when it turns right, and identifies "information type D214" when it turns left, respectively; subsequently, it relates these types to character string data D121 to D141 input in this case, respectively. Thus, the character string data D121 to D141 to which the information types D212 to D214 are related are defined as medical data D12 to D14, respectively.

Further, while inputting the sound data, the mobile terminal M1 may be operated with its direction changed. In such a case, at first, the association processor 14 identifies the timing point at which the state is changed (the direction in the mobile terminal M1 is changed) based on the information indicating the timing point related to the state information received from the state detector 12. Next, the association processor 14 refers to the information indicating the timing point related to the character string data received from the sound analyzer 11, and divides the character string data at the part corresponding to the identified timing point. Hereinafter, similar to the above-described operation, the association processor 14 identifies the information type based on the state information corresponding to the identified timing point for each of the divided character string data, and relates the identified information type to the corresponding character string data. As a result of this operation, even when the direction of the mobile terminal M1 (namely, the state of the mobile terminal Ml) is changed during sound input, it becomes possible to generate medical data for each state of the mobile terminal M1.

The association processor 14 outputs the character string data to which the information type is related, namely, the medical data, to the medical information update part 15.

The medical information update part 15 receives medical data from the association processor 14. In addition, the medical information update part 15 stores the template of a medical record having a plurality of regions in advance. Each region included in this template is related to a specific information type in advance. The medical information update part 15 extracts the character string information from the medical data received from the association processor 14. In addition, the medical information update part 15 refers to the information type included in the medical data, and writes the extracted character string information in the region corresponding to the information type. Thereby, data of the medical record (hereinafter, merely referred to as "medical record") is created. The medical information update part 15 stores the created medical record in the medical information storage 30. The medical information storage 30 is storage for storing medical records (namely, medical information).

Further, the medical information update part 15 may be operated so as to update the medical records stored in advance in the medical information storage 30. In this case, the association processor 14 receives the identification information (for example, patient ID, examination ID, etc.) for identifying the medical record to be updated from the operator, and this identification information may be related to the medical data. The medical information update part 15 retrieves the medical information storage 30 based on this identification information. Then, if the corresponding medical record exists, this medical record may be extracted for updating. In addition, if there is no corresponding medical record, by newly creating a medical record, the medical information update part 15 may relate this identification information to the created medical record and store it in the medical information storage 30. Hereinafter, a description will be provided assuming that the medical information update part 15 relates the identification information to each medical record and stores it in the medical information storage 30.

The medical information extractor 21 receives the designation of the medical record (for example, identification information of the medical record) via the operation part 232 from the operator. The medical information extractor 21 retrieves the medical information storage 30 and extracts the designated medical record. The medical information extractor 21 outputs the extracted medical record to the display controller 22.

The display controller 22 receives the medical record from the medical information extractor 21. The display controller 22 displays this medical record on the display 231 in a specific display manner.

In addition, upon receiving the state information from the state detector 12, the display controller 22 may switch the input screen for inputting the medical information in accordance with the state information. Specifically, the display controller 22 receives the state information from the state detector 12, compares this with the determination information stored in the determination information storage 13, and identifies the information type (for example, "main complaint," "findings," "assessment," and "planning"). The display controller 22 stores the input screen in advance for each information type, and causes the display 231 to display the input screen corresponding to the identified information type. An example of the input screen is illustrated in FIG. 3A and FIG. 3B.

Figure 3A:
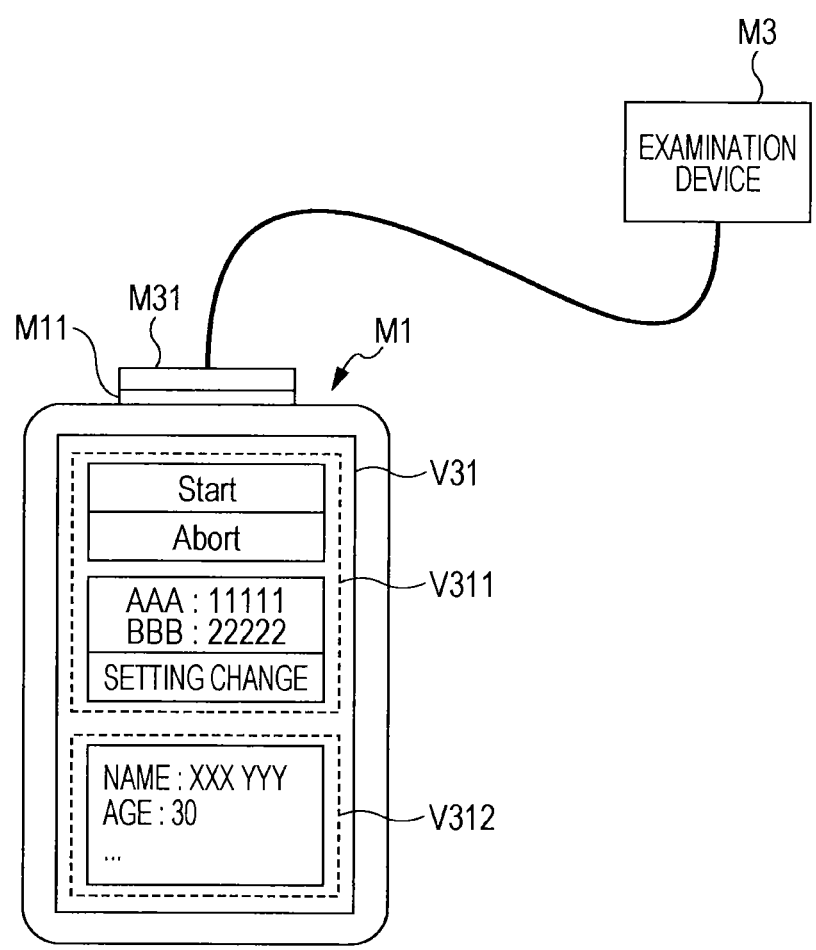
FIG. 3A illustrates an example of the operational screen.

For example, FIG. 3A illustrates an example of an input screen V31 for using an examination device M3 together and inputting "findings." The input screen V31 is used in the case of connecting a connection terminal M31 of the examination device M3 to a connection terminal M11 of an external device of the mobile terminal M1, and inputting the findings to the data obtained by the examination device M3 (for example, medical images). Therefore, the input screen V31 is related to the state information when the connection terminal M11 is positioned on the upper side. The input screen V31 includes, for example, an operation interface V311 for operating the examination device M3, the obtained data, and examination information V312 of the examination via which the data is obtained.

Figure 3B:
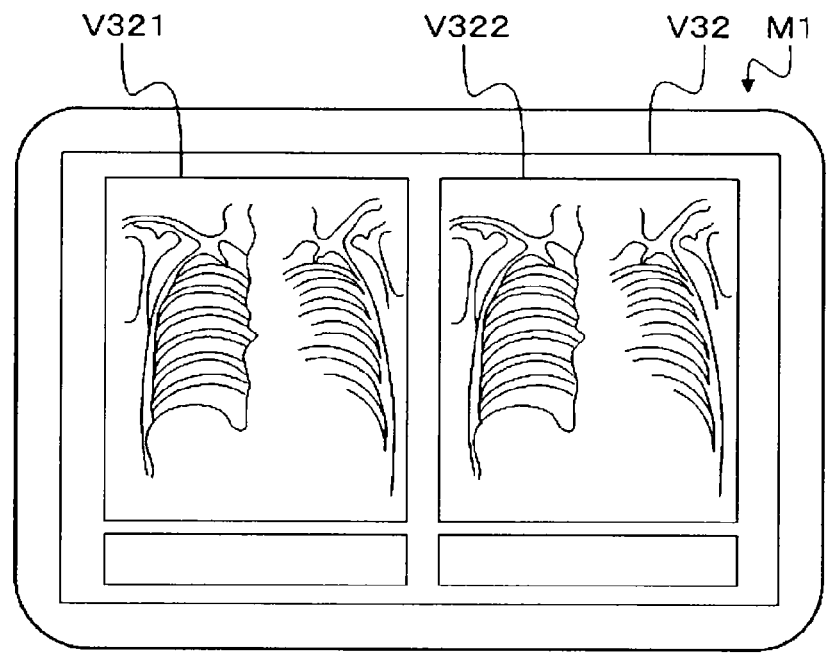
FIG. 3B illustrates an example of the operational screen.

In addition, FIG. 3B illustrates an example of an input screen V32 for inputting an "assessment" while comparing a plurality of medical images with each other. The input screen V32 displays a plurality of medical images at the same time, and inputs the assessment results while comparing these images with each other. In the example of FIG. 3B, on the input screen V32, the medical images V321 and V322 are displayed as being laterally arranged. Thus, the input screen V32 is related to the state information when the screen is arranged sideways and the lateral width of the screen is wider so as to be capable of displaying at least two medical images laterally. Thus, according to the method of using the mobile terminal M1 at each scene, the input screen and the state information may be related with each other.

As described above, the place on which each above-described configuration is placed is not limited if it can carry out its function, and it may be disposed in either of the mobile terminal M1 or the medical information management server M2. In addition, all of the above-described configurations may be included in the mobile terminal M1. In this case, separately establishing communication between the mobile terminal M1 and the medical information management server M2, the mobile terminal M1 may be operated such that the medical record stored in the medical information storage 30 is transferred to the medical information management server M2.

Further, in the above description, an example is described, in which, based on the medical data, a medical record is created which is stored in the medical information storage 30; however, the mobile terminal M1 may be operated such that the medical data is stored in the medical information storage 30. In this case, for example, based on the medical data stored in the medical information storage 30, a configuration such that a medical record is created may be separately provided.

Figure 4:
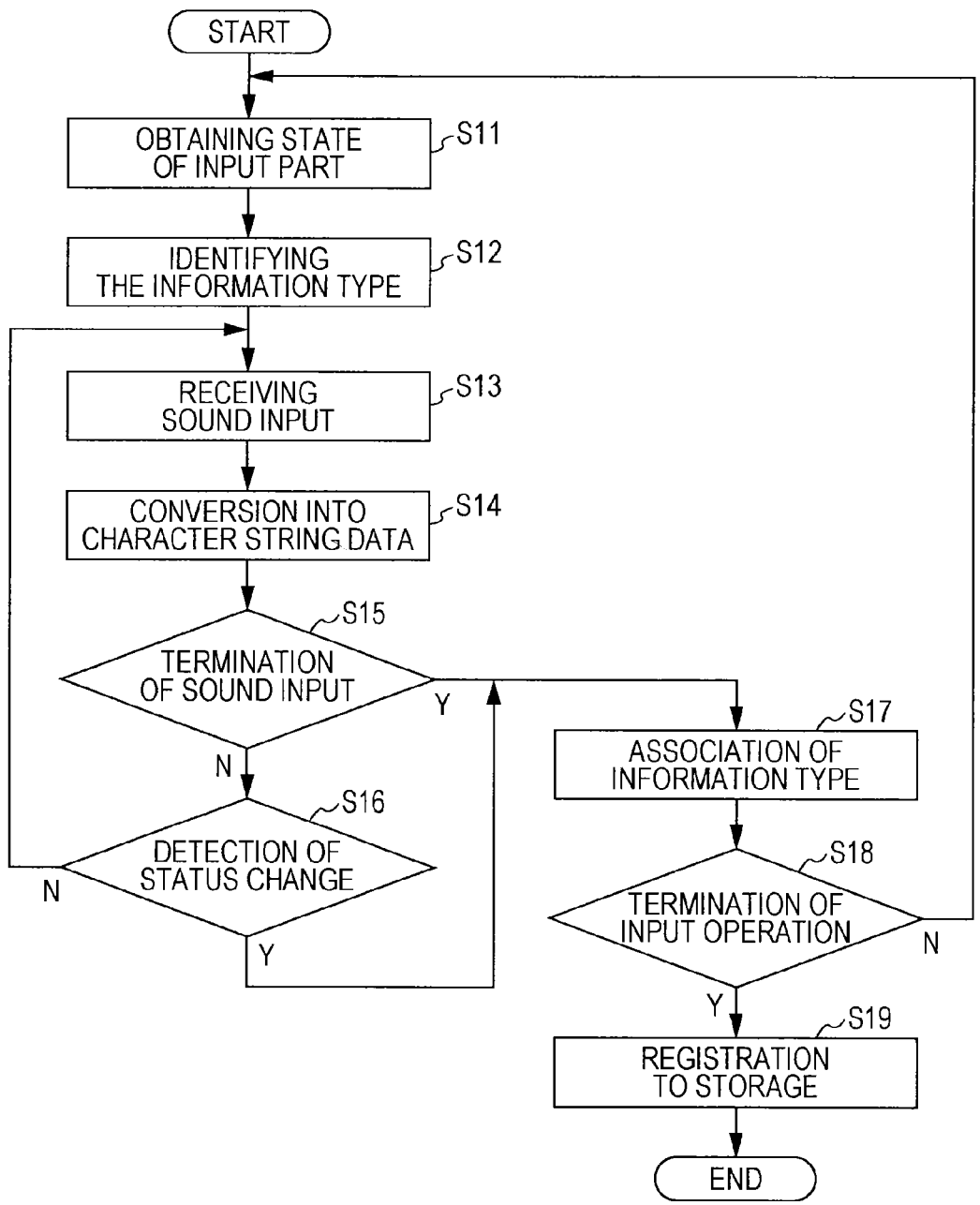
FIG. 4 is a flow chart illustrating the sequence of operations related to the input of medical information into the medical information processing system according to the embodiment.

Next, in the medical information processing system according to the present embodiment, a sequence of processing flows from the time a medical record is generated based on the sound-input medical information until the generated medical record is stored in the medical information storage 30 will be described with reference to FIG. 4. FIG. 4 is a flow chart illustrating the sequence of operations related to the input of medical information into the medical information processing system.

(Step S11)

The state detector 12 detects the physical direction of the mobile terminal M1. Specifically, in the mobile terminal M1, a gyro, a vibration sensor, an acceleration sensor, etc. are incorporated. Thereby, the state detector 12 analyzes the outputs of these sensors, and detects the physical direction of the mobile terminal M1. The state detector 12 relates the information indicating a timing point upon receiving the output of each sensor indicating the physical direction to the state information indicating the physical direction of the detected mobile terminal M1 (namely, the state of the mobile terminal M1). The state detector 12 outputs the state information to which the information indicating the timing point is related to the association processor 14.

(Step S12)

The association processor 14 receives the state information from the state detector 12. The association processor 14 compares the state information with determination information stored in the determination information storage 13, and identifies the information type corresponding to this state information.

(Step S13)

The sound input part 233 outputs the sound data input from the operator to the sound analyzer 11. The sound analyzer 11 receives the sound data from the sound input part 233.

(Step S14)

The sound analyzer 11 analyzes this sound data and converts it into character string data. The sound analyzer 11 relates information indicating the timing point upon receiving the sound data as the generation origin of the character string data to the generated character string data. The sound analyzer 11 outputs the character string data to which the information indicating the timing point is related to the association processor 14.

(Step S15, Step S17)

When the sound input is ended (Step S15, Y), the association processor 14 receives character string data from the sound analyzer 11. In addition, the association processor 14 receives state information from the state detector 12. The association processor 14 compares the state information with the determination information stored in the determination information storage 13, and identifies the information type corresponding to this state information. The association processor 14 relates the identified information type to the character string data. The association processor 14 outputs the character string data to which the information type is related, namely, the medical data, to the medical information update part 15.

(Step S15, Step S16)

For the case in which sound input is continued (Step S15, N) and changes in the state of the mobile terminal M1 are not detected (Step S16, N), the sound analyzer 11 receives the sound data from the sound input part 233, and continues the processing for converting the sound data into character string data. The medical information update part 15 receives the medical data from the association processor 14.

(Step S15, Step S16, Step S17)

In the state in which the sound input is continued (Step S15, N) and for the case in which changes in the state of the mobile terminal M1 are detected (Step S16, Y), the association processor 14 receives the character string data from the sound analyzer 11. In addition, the association processor 14 receives the state information from the state detector 12.

Next, at first, the association processor 14 identifies the timing point when the state is changed (the direction of the mobile terminal M1 is changed) based on the information indicating the timing point related to the state information received from the state detector 12. Hereinafter, similar to the above-described operation, the association processor 14 identifies the information type based on the state information corresponding to the identified timing point for each of the divided character string data, and relates the identified information type to the corresponding character string data. The association processor 14 outputs the character string data to which the information type is related, namely, the medical data, to the medical information update part 15. The medical information update part 15 receives the medical data from the association processor 14.

(Step S18)

The above-described processing is carried out as long as the input operation by the operator is continued (Step S18, N).

(Step S19)

If the input operation by the operator is ended, the medical information update part 15 creates a medical record based on the received medical data. Specifically, the medical information update part 15 stores a template of a medical record having a plurality of regions in advance. Each region included in this template is related to a specific information type in advance. The medical information update part 15 extracts the character string information from the medical data received from the association processor 14. In addition, the medical information update part 15 refers to the information type included in this medical data, and writes the extracted character string information in the region corresponding to this information type. Thereby, a medical record is created. The medical information update part 15 stores the created medical record in the medical information storage 30.

As described above, in the medical information processing system according to the present embodiment, based on the direction of the mobile terminal M1, the type of medical information is identified and the medical information to be input via sound input is received. Thereby, the operator can specify the type of medical information to be input via sound input without operating a small screen. Thus, according to the medical information processing system of the present embodiment, without carrying out troublesome procedures such as screen operation to the small screen, the type of the medical information to be input can be specified via a simple operation.

MODIFIED EXAMPLE 1

Next, a medical information processing system according to Modified Example 1 will be described. In the above-described embodiment, the type of the medical information input at that time was recognized in accordance with the physical direction of the mobile terminal M1. However, if the type of medical information can be recognized in accordance with a plurality of states of the mobile terminal M1, recognition of the type is not always limited to recognition based on the direction of the mobile terminal. The medical information processing system according to Modified Example 1 recognizes the type of medical information in accordance with the connection state between the mobile terminal M1 and the external device that is different from the mobile terminal M1, namely, the presence or absence of a connection between the mobile terminal M1 and the external device, and the type of connected external device. Hereinafter, the specific configuration of the medical information processing system according to Modified Example 1 will be described focusing on the points different from the above-described embodiment.

A state detector 12 according to Modified Example 1 is provided with a communication function, and due to this communication function, the state detector 12 detects the connection state between the mobile terminal M1 and the external device (for example, whether or not a connection is established). Then, when the connection between the state detector 12 and the external device is established, the state detector 12 detects the type of external device connected thereto. For example, when a connection between the state detector 12 and the external device is established, receiving the control information indicating the type from the external device, the type of external device may be determined based on this. As the external device, for example, an examination device M3 such as an ultrasonic diagnostic apparatus, a verifier for verifying a patient, an imaging device for imaging a medical interview and a conference, etc. are considered. The state detector 12 outputs the information indicating the connection state with the detected external device to the association processor 14 as the state information.

The determination information storage 13 stores the state information (namely, the information indicating the connection state between the mobile terminal M1 and the external device) and the information type indicating the type of information (for example, "main complaint," "findings," "assessment," and "planning") as the determination information while relating these information types with each other in advance.

As an example of this association, for example, in the step of "main complaint" to accept a complaint of a patient, recognition of the patient is carried out. As a result, the state in which the mobile terminal M1 is connected to the verifier may be related to the information type indicating "main complaint." In addition, in the step of "findings," findings in the medical data such as a medical image, etc. obtained by the examination device M3, etc. are input. Consequently, the state in which the mobile terminal M1 is connected to the examination device M3 may be related to "findings." In addition, in the step of "planning," the manner in which an attending doctor provides an explanation of an examination and the planning of a therapy to the patient is sometimes photographed with a camera, etc. Therefore, for example, the state in which an imaging apparatus such as a camera is connected to the mobile terminal M1 may be related to "planning." In addition, as in the step of "assessment," in the case capable of carrying out the operation without using the external device, the state in which the external device is not connected to the mobile terminal M1 (namely, the state in which a connection is not established) may be related to the information type.

The association processor 14 receives the character string data from the sound analyzer 11. The association processor 14 receives the state information from the state detector 12. The association processor 14 compares the state information with the determination information stored in the determination information storage 13, and then identifies the information type corresponding to the state information. The association processor 14 relates the identified information type to this character string data.

Not limited to the communication state, for example, the type of medical information may be recognized in accordance with the state of the operation of the connected device (hardware or software). A specific explanation will be provided using an ultrasonic diagnostic apparatus as an example. For example, "the state of carrying out scan," "the state of displaying ultrasonic images," "the state of inputting information such as patient information," etc. are considered. "The state of carrying out scanning" may be determined, for example, depending on the information indicating the presence or absence of the setting information upon scanning, information indicating the mode of carrying out scanning, etc. "The state of displaying the ultrasonic images," "the state of inputting the information such as patient information," etc. may be determined based on the information indicating these operational modes (for example, a display/input mode of patient information, a measurement mode of the ultrasonic images, etc.).

As described above, according to the medical information processing system of Modified Example 1, in accordance with the connection state to the external device, the type of medical information to be input at this time is identified. Thereby, the operator can specify the type of medical information to be input via sound input without operating the small screen. Thus, also according to the medical information processing system of Modified Example 1, without carrying out troublesome procedures such as screen operation to the small screen, the type of the medical information to be input can be specified via a simple operation.

MODIFIED EXAMPLE 2

Figure 5:
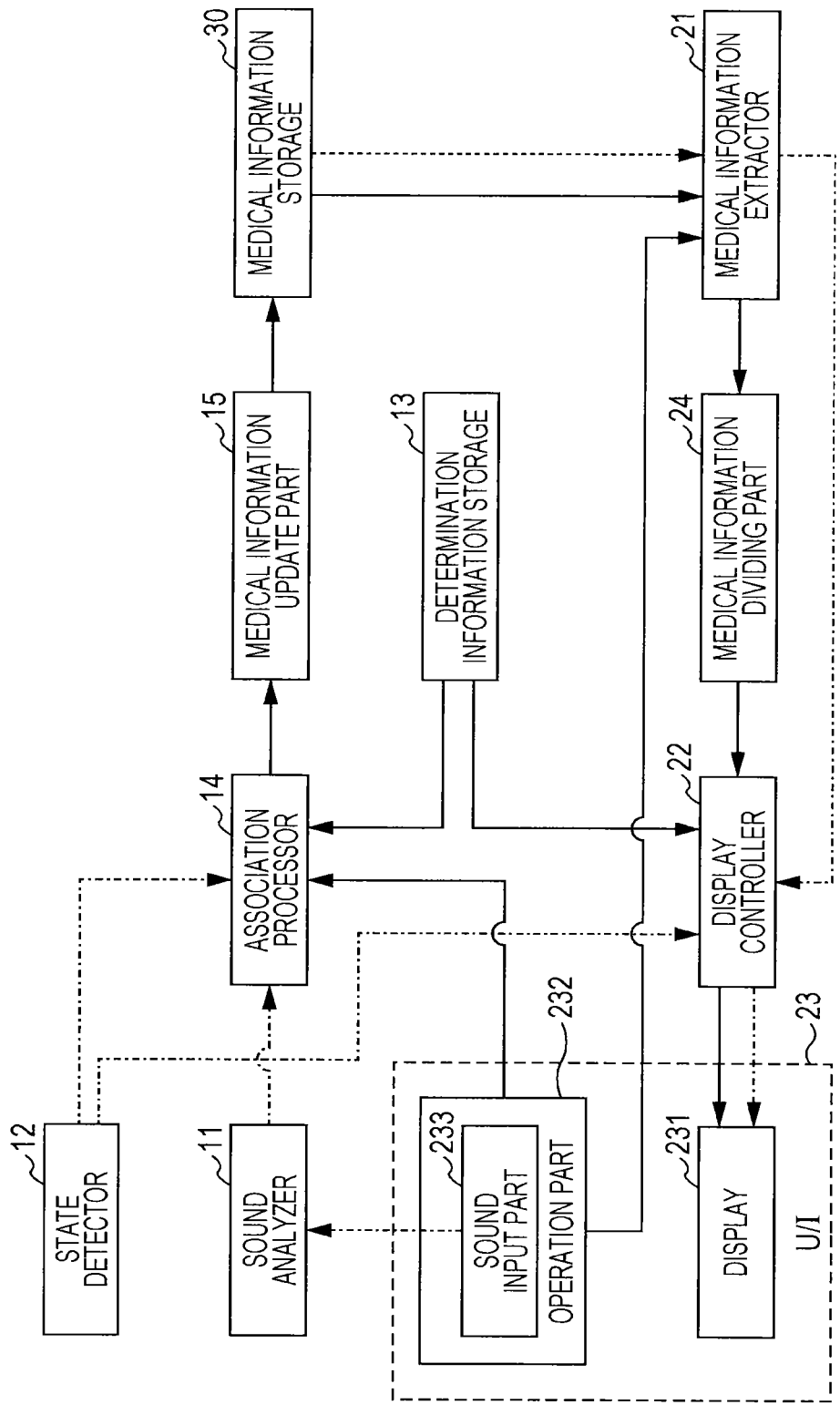
FIG. 5 is a block diagram of the medical information processing system according to Modified Example 2.
Figure 6:
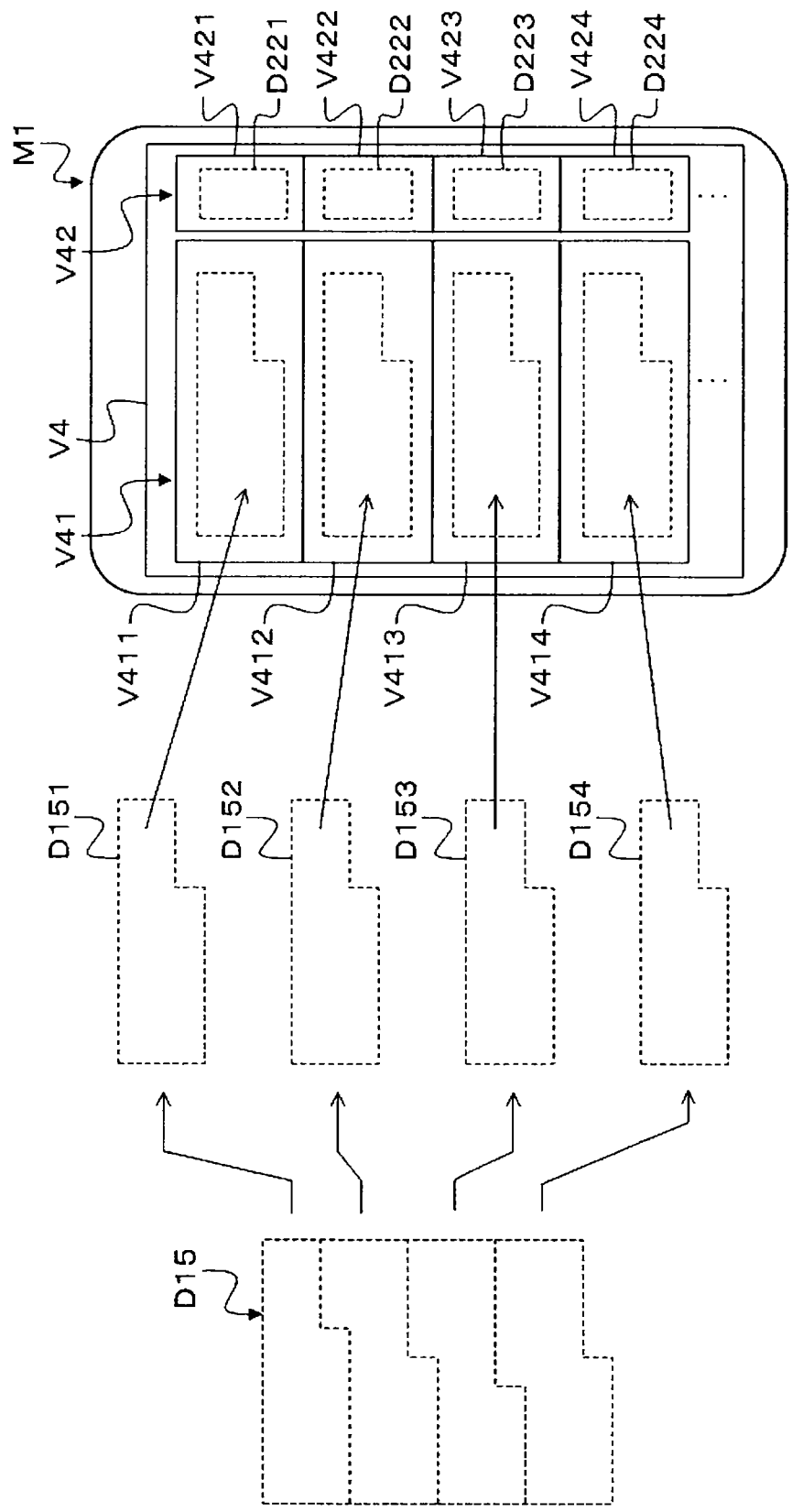
FIG. 6 illustrates an example of the operation of the medical information processing system according to Modified Example 2.

Next, a medical information processing system according to Modified Example 2 will be described with reference to FIG. 5 and FIG. 6. FIG. 5 is a block diagram of the medical information processing system according to Modified Example 2. In addition, FIG. 6 is a conceptual drawing illustrating an example of the operation of the medical information processing system according to Modified Example 2. The medical information processing system according to Modified Example 2 changes the type of at least part of the description of the medical records stored in the medical information storage 30 into another type. Thereby, it becomes possible to shift part of the medical information input in a desired region upon creating a medical record to another region. Further, the processing according to the creation of a medical record is similar to the above-described embodiment and Modified Example 1. Therefore, hereinafter, the detailed configuration of the medical information processing system according to Modified Example 2 will be described focusing on changes in the type of medical information different from the above-described embodiments.

The medical information extractor 21 receives a designation of the medical record (namely, a designation of the part of the medical record that changes the type of description) via the operation part 232 from the operator. The medical information extractor 21 retrieves the medical information storage 30 and extracts the designated medical record. The medical information extractor 21 outputs the extracted medical record to the display controller 22.

The display controller 22 receives the medical record from the medical information extractor 21. The display controller 22 causes the display 231 to display this medical record in a specific display manner. The operation for displaying this medical record is similar to the above-described embodiment.

Next, the operation part 232 receives the designation of the description in the displayed medical record regarding which type should be changed. In this case, the operation part 232, for example, receives the designation of the region configuring the medical record, and may recognize the medical information described in this region as the designated description, or it receives the designation of the appropriate region via a drag operation, etc., and may recognize this region as the designated description. The operation part 232 notifies the medical information extractor 21 of the information indicating the appropriate region (for example, the positional information in the appropriate region in the medical record) based on this designation.

The medical information extractor 21 receives the information indicating the appropriate region designated by the operator via the operation part 232. The medical information extractor 21 extracts the description in the medical record corresponding to the information indicating the appropriate region as character string data via the display controller 22 from the medical record displayed by the display 231. The medical information extractor 21 outputs the extracted character string data to the medical information dividing part 24 together with the identification information indicating the medical record that is the extraction origin.

The medical information dividing part 24 receives the extracted character string data and the identification information indicating the medical record from the medical information extractor 21. The medical information dividing part 24 analyzes this character string data and divides it into a specific unit (for example, a segment, a paragraph, etc.). Here, it is assumed that the medical information dividing part 24 divides the character string data into partial character string data for each sentence. Here, FIG. 6 will be referred. D15 in FIG. 6 illustrates the character string data extracted by the medical information extractor 21. Hereinafter, a description will be provided assuming that, as illustrated in FIG. 6, the medical information dividing part 24 divides the character string data D15 into partial character string data D151 to D154. The medical information dividing part 24 outputs the partial character string data D151 to D154 to the display controller 22 together with the identification information indicating the medical record.

The display controller 22 receives the partial character string data D151 to D154 and the identification information indicating the medical record from the medical information dividing part 24. The display controller 22 generates an operational screen V4 for designating the type of information with respect to each of these partial character string data D151 to D154. The operational screen V4 includes, as illustrated in FIG. 6, a region V41 for displaying the partial character string data and a region V42 for designating the type of information. The region V41 is provided with a plurality of partial regions V411 to V414. The medical information dividing part 24 and the received partial character string data D151 to D154 are displayed on the partial regions V411 to V414. In addition, the region V42 includes partial regions V421 to V424. In addition, the partial region V421 is related to the partial region V411, the partial region V422 is related to the partial region V412, the partial region V423 is related to the partial region V413, and the partial region V424 is related to the partial region V414, respectively.

The display controller 22 causes the display 231 to display the operational screen V4 that displays the information type on the partial regions V421 to V424 such that the information type can be input. In this case, referring to the determination information storage 13, the display controller 22 may generate an operational screen V4 so as to be capable of selecting only the information type registered in advance. Thereby, the operator can designate the information type with respect to each of the partial character string data D151 to D154 displayed on the partial regions V411 to V414 via the operation part 232. Hereinafter, a description will be provided with the information type input in the partial regions V421 to V424 as the information types D221 to D224. Further, the display controller 22 may notify the U/I23 of the identification information of the medical record that is the extraction origin of the partial character string data D151 to D154 together with the operational screen V4. Thereby, the U/I23 can recognize the medical record that is the extraction origin of the partial character string data D151 to D154 displayed on the operational screen V4.

Receiving the operation to the operational screen V4 by the operator, the operation part 232 relates the information type (namely, the information types D221 to D224) input in the partial regions V421 to V424 to the partial character string data (namely, any of the partial character string data D151 to D154) that correspond to each of the information types. Specifically, for example, the operation part 232 relates the information type D221 input in the partial region V221 to the partial character string data D151 displayed in the partial region V411 related to the partial region V221. The same also applies to the information types D222 to D224 and the partial character string data D152 to D154. The operation part 232 outputs each of the partial character string data to which the designated information type is related to the association processor 14 together with the identification information indicating the medical record to be updated (namely, the identification information indicating the medical record notified from the display controller 22). Further, the subsequent operations will be described taking the partial character string data D151 to which the information type D221 is related as an example.

The association processor 14 receives the partial character string data D151 to which the information type D221 is related and the identification information indicating the medical record to be updated from the operation part 232. The association processor 14 outputs the partial character string data D151 to which this information type D221 is related as the medical data D16 together with the identification information indicating the medical record to the medical information update part 15.

The medical information update part 15 receives the medical data D16 and the identification information indicating the medical record from the association processor 14. The medical information update part 15 extracts the medical record corresponding to the received identification information from the medical information storage 30. Referring to the information type D221 included in the medical data D16, the medical information update part 15 identifies the region related to this information type D221 in the medical records. The medical information update part 15 extracts the partial character string data D151 from the medical data D16, and updates the medical information input in the identified region in the medical record with this partial character string data D151. In this case, the medical information update part 15 may add the partial character string data D151 already input in this region to the medical information, or it may overwrite the medical information already input in this region with the partial character string data D151. In addition, upon displaying the operational screen V4, displaying the existing medical record together, it may be possible to designate the part into which the partial character string data D151 is inserted. In this case, the medical information update part 15 may insert the partial character string data D151 in the designated place in the identified region.

As described above, according to the medical image managing system of Modified Example 2, it becomes possible to update the above-described embodiment and the medical record generated and updated by Modified Example 1 via a simple operation.

Several embodiments of the present invention have been described, but these embodiments have been presented as examples and are not intended to limit the scope of the invention. These new embodiments may be implemented in various other modes, and various omissions, substitutions, and changes may be made within the scope of the substance of the invention. These embodiments and modifications thereof are included in the scope and substance of the invention and are also included in a scope equivalent to that described in the scope of patent claims.

What is claimed is:

1. A medical information processing system for inputting medical information, comprising:
    a terminal device including an input configured to receive medical information via sound input and at least one sensor indicating a physical direction of the terminal device;
    a sound analyzer configured to receive the sound input from the input of the terminal device and to analyze the received sound and convert the analyzed sound into character information;
    a state detector configured to detect a physical state of the terminal device;
    a determination information storage configured to store in advance determination information in which a plurality of physical states with respect to the terminal device are related to each type of a plurality of parts making up a medical record;
    an association processor configured to identify the type corresponding to the physical state of the detected terminal device based on the determination information, and relating the information indicating the identified type with the character information converted from the sound input, and
    a display controller configured to display an input screen corresponding to a type of the determination information that identifies the information type corresponding to the physical state of the detected terminal device based on the medical record, wherein
    the state detector obtains at least one of a physical direction of the terminal device based on the sensor information from the terminal device, presence or absence of a connection between the terminal device and another device and, if present, a connection state based on a type of the another device and information on an operational state of the another device received therefrom.

2. The medical information processing system according to claim 1,
    wherein the medical record includes a plurality of recording regions, and each of the plurality of recording regions has been related in advance to any of the information indicating the type, and
    the medical information processing system further comprises an update part configured to generate or update the medical record by writing the character information in the recording region related to the type in turn related to the character information.

3. The medical information processing system according to claim 1,
    wherein the information of the operational state is any one of a state in which the device carries out scanning, a state in which the device displays ultrasonic images, and a state in which patient information is input into the device.

4. The medical information processing system according to claim 1, further comprising an edit processor configured to change the relation between the information corresponding to the type and the character information converted from the sound input based on the input of an operator.

* * * * *